United States Patent [19]
Battersby et al.

[11] Patent Number: 6,165,716
[45] Date of Patent: Dec. 26, 2000

[54] SCREENING FOR DISORDERS OF SEROTONERGIC DYSFUNCTION

[75] Inventors: Sharon Battersby; George Fink; Guy Manning Goodwin; Anthony John Harmar; Alan David Ogilvie; Christopher Albert Dale Smith, all of Edinburgh, United Kingdom

[73] Assignee: Medical Research Council, London, United Kingdom

[21] Appl. No.: 09/043,507

[22] PCT Filed: Sep. 23, 1996

[86] PCT No.: PCT/GB96/02360

§ 371 Date: Sep. 3, 1998

§ 102(e) Date: Sep. 3, 1998

[87] PCT Pub. No.: WO97/11175

PCT Pub. Date: Mar. 27, 1997

[30] Foreign Application Priority Data

Sep. 23, 1995 [GB] United Kingdom .................... 9519458
Oct. 3, 1995 [GB] United Kingdom .................... 9520113
Jun. 1, 1996 [GB] United Kingdom .................... 9611473

[51] Int. Cl.[7] ............................. C12Q 1/08; C07H 21/02; C07H 21/04
[52] U.S. Cl. .............................. 435/6; 536/23.1; 536/23.5
[58] Field of Search ................................. 536/23.1, 23.5; 435/6

[56] References Cited

FOREIGN PATENT DOCUMENTS

93/08261 4/1993 WIPO .

OTHER PUBLICATIONS

Diagnostic and Statistical Manual of Mental Disorders, Fourth Edition, Published by American Psychiatric Association, Washington D.C. p. 317–318, 1994.

Parsian et al., American Journal of Medical Genetics, vol. 54(1), p. 5–7, Mar. 1994.

Ogilvie et al., "Polymorphism in serotonin transporter gene associated with susceptibility to major depression", Lancet, vol. 347, Mar. 16, 1996, pp. 731–733.

Collier et al., "The serotonin transporter is a potential susceptibility factor for bipolar affective disorder", Neuroreport, vol. 7, No. 10, Jul. 8, 1996, pp. 1675–1679.

Lesch et al., "Organization of the human serotonin transporter gene", Journal of Neural Transmission, vol. 95, 1994, pp. 157–162.

*Primary Examiner*—Deborah J. Clark
*Assistant Examiner*—Shin-Lin Chen
*Attorney, Agent, or Firm*—Ratner & Prestia

[57] ABSTRACT

Three novel alleles of the serotonin transporter gene are disclosed and shown to be effective markers for screening and diagnosis of migraine and psychiatric disorders. The sequences of the alleles are given. Methods for in vitro screening of individuals using DNA taken from blood samples are taught.

6 Claims, 6 Drawing Sheets

| | | | | | |
|---|---|---|---|---|---|
| Lesch 10 | GGCTGTGACCCGAGGTG | GGCTGTGACCCGGGGTG | GGCTGTGACCCGGGGTG | GGCTGTGACCCGGGGTG | GGCTGCGACCTGGGGTG |
| STin2.9  | GGCTGTGACCCAGGGTG | GGCTGTGACCCGGGGTG | GGCTGTGACCCGGGGTG | GGCTGTGACCCGGGGTG | GGCTGCGACCTGGGGTG |
| STin2.10 | GGCTGTGACCCAGGGTG | GGCTGTGACCCGGGGTG | GGCTGTGACCCGGGGTG | GGCTGTGACCCGGGGTG | GGCTGCGACCTGGGGTG |
| STin2.12 | GGCTGTGACCCAGGGTG | GGCTGTGACCCGGGGTG | GGCTGTGACCCGGGGTG | GGCTGTGACCCGGGGTG | GGCTGCGACCTGGGGTG |
| | 1 (A) | 2 (B) | 3 (C) | 4 (D) | 5 (E) |

| | | | | | |
|---|---|---|---|---|---|
| Lesch 10 | .................. | .................. | GGCTGTGACCTGGGGTG | GGCTGTGACCCGGGGTG | GGCTGTGACCCGGGGTG |
| STin2.9  | GGCTGTGACCTGGGATG | .................. | .................. | GGCTGTGACCC.GGGTG | GGCTGTGACCC.GGGTG |
| STin2.10 | GGCTGTGACCTGGGATG | GGCTGTGACCC.GGGTG | GGCTGTGACCTGGGGTG | GGCTGTGACCC.GGGTG | GGCTGTGACCC.GGGTG |
| STin2.12 | GGCTGTGACCTGGGATG | GGCTGTGACCC.GGGTG | GGCTGTGACCTGGGGTG | GGCTGTGACCC.GGGTG | GGCTGTGACCC.GGGTG |
| | 6 (F) | 7 (D) | 8 (G) | 9 (D) | 10 (G) |

| | | |
|---|---|---|
| Lesch 10 | GGCTGTGACCCGGGGTG | GGCTGTGACCTGGGATG |
| STin2.9  | GGCTGTGACCC.GGGTG | GGCTGTGACCTGGGATG |
| STin2.10 | GGCTGTGACCC.GGGTG | GGCTGTGACCTGGGATG |
| STin2.12 | GGCTGTGACCC.GGGTG | GGCTGTGACCTGGGATG |
| | 11 (D) | 12 (G) |

Fig. 1

SCREENING FOR DISORDERS OF SEROTONERGIC DYSFUNCTION

This is a 371 of application Ser. No. PCT/GB96/02360, filed Sep. 23, 1996.

The present invention relates to a method of screening for and for diagnosis of psychiatric disorders and other disorders of serotonergic function, for example migraine.

Serotonin (5-hydroxytryptamine or 5-HT) is known to be involved in brain function and activity. The serotonin transporter (also known as 5-HTT) has been targeted using highly selective drugs to effectively treat depressive illness and anxiety disorders (see Anderson et al, J Psychopharmacol 1994 8; 238–249).

The structure of the rat serotonin transporter cDNA was published in 1991 (Blakely et al, Nature 1991 354, 66–70; and Hoffman et al, Science 1991 254, 578–580) and U.S. Pat. No. 5,418,162 is directed to the sequence of the cDNA for the rat serotonin transporter and its use as an oligonucleotide probe which could be used as a PCR extension primer. The corresponding human cDNA was reported by Lesch et al, Journal of Neural Transmission 91; 68–73 1993 and separately by Ramamoorthy et al, in Proceedings of the National Academy of Sciences, USA, 19; 2542–2546 1993.

The structure and arrangement of the human serotonin transporter gene was first published in 1994 by Lesch et al (Journal of Neural Transmission 95; 157–162). The authors noted the existence of a "17 bp repetitive element" as a variable number tandem repeat (VNTR) which occurred in the second intron of the gene. The sequence data for the VNTR is available in the Genbank/EMBL databases under accession number X76754 and is reproduced as part of FIG. 1. Lesch et al noted that the majority of the chromosomes examined had either 10 or 11 copies of the repeat and for such samples the frequency of the 10 VNTR sequence was 0.47 with 41% of individuals displaying heterogeneity. It was speculated that the number of repeats could possibly play a role in the pathogenesis of neuropsychiatric illness. To date no evidence has been reported which definitively links the VNTR sequences with any particular function.

The human serotonin transporter gene is localised to chromosome 17q11.1–q12 (see Ramamoorthy et al 1993 supra) and to date there is no published evidence for genetic linkage of any affective disorder to this part of the genome. Current data indicates that, while there is a genetic basis for psychiatric disorders such as anxiety and depression, and also for migraine, there is no evidence which convincingly demonstrates an underlying molecular basis for genetic susceptibility in either case.

For example, a study made by Lesch et al in 1995 (Biological Psychiatry 37; 215–223) in which 17 patients suffering from major depressive or bipolar disorder were screened for mutations in the serotonin transporter cDNA sequence showed no difference compared to the four controls.

The studies leading to the present invention have surprisingly found 3 alleles of the VNTR region in intron 2 of the serotonin transporter gene. The 3 alleles located are all novel and are designated STin2.9, STin2.10 and STin 2.12 containing 9, 10 and 12 copies of the VNTR repeat, respectively. The third allele (STin 2.10) containing 10 copies of the repeat differs from that described previously by Lesch et al (1994, supra). No individuals possessing 11 copies of the repeat were identified.

The frequencies of the different allele forms were compared between the control group and groups having a major affective disorder. There was a significant difference between the control and affective disorder groups. In particular the presence of the STin2.9 allele was found to be significantly associated with affective disorder and was most common in unipolar patients. This is the first time that a genetic variation at the level of DNA sequence in a candidate gene has been positively associated with affective disorders.

Thus, the present invention provides the novel alleles STin2.9, STin2.10 and STin2.12. The sequence of each of the alleles STin2.9, STin2.10 and STin2.12 are presented in FIG. 1, labelled accordingly and compared to the 10 repeat sequence reported by Lesch et al, 1994, supra. The present invention also provides a polynucleotide having a sequence substantially as set out in FIG. 1 for the alleles STin2.9, STin2.10 or STin2.12 or a part thereof. The present invention encompasses these alleles or the polynucleotides in vectors and in transformed cells. Likewise the present invention incorporates the use of such alleles, polynucleotides, derivatives or parts thereof in genetic engineering procedures (for example as probes for PCR).

In a further aspect, the present invention provides a cell line (preferably a mammalian cell line and particularly a human cell line) comprising at least one of the alleles STin2.9, STin2.10 or STin2.12 or a polynucleotide having a sequence substantially as set out for one of those alleles in FIG. 1.

The sequences of alleles STin2.9, STin2.10 and STin2.12 are also presented in the sequence listing as SEQ ID Nos 1, 2 and 3 respectively.

Generally the allele or polynucleotide will be located in intron 2 of at least part of the serotonin transporter gene.

Likewise the present invention includes a transgenic animal which contains novel alleles and sequences according to the present invention. Generally the transgenic animal will be a mammal, especially a laboratory animal for example a rat or mouse.

The cell line (which may be a transformed cell line) and transgenic animal according to the present invention may each independently be used as a model to evaluate potential agents which may be effective for combatting psychiatric disorders and other disorders of serotonergic function, for example migraine.

There exists in the art numerous publications describing how to form such vectors, transformed cell and transgenic animals. Reference may be made to "Principles of Gene Manipulation" Old and Primrose, 5th edition, 1995, Blackwell Scientific Publications (and the references therein) as providing a general background to the subject.

In a yet further aspect, therefore, the present invention provides a method of evaluating agents for the ability to influence the expression of the serotonin transporter, said method comprising exposing a cell line or transgenic animal as described above to said agent and determining the effect of said agent on the expression of the serotonin transporter.

In another aspect the present invention provides a method of diagnosis of psychiatric disorders, said method comprising analysing the number of VNTR repeats in the second intron of the serotonin transporter gene.

In a further aspect, the present invention provides a method of diagnosis of an individual's susceptibility to migraine, said method comprising analysing the number of VNTR repeats in the second intron of the serotonin transporter gene.

Advantageously such methods of the present invention will look particularly for the alleles STin2.9, STin2.10 and STin2.12, and especially for STin2.9.

Viewed from a further aspect the present invention provides a method of screening individuals for the potential to develop a psychiatric disorder or to suffer from migraine, said method comprising analysing the number of VNTR repeats in the second intron of the serotonin transporter gene.

Advantageously such methods of the present invention will look particularly for the alleles STin2.9, STin2.10 and STin2.12, and especially for STin2.9.

Particular psychiatric disorders which may be diagnosed and screened for using the methodology as mentioned above include, from the DSM-IV taxonomy, mood disorders, anxiety disorders and personality disorders. The particular disorders of interest (DSM-IV codes in parentheses) are depressive disorders (296.XX, 296.2X, 296.3X, 300.4, 311), and particular anxiety disorders (300.01, 300.21, 300.22, 300.23, 300.3, 300.02, 300.00), personality disorders (301.83, 301.4) and general medical disorders characterised by abnormal serotonergic function including migraine and irritable bowel syndrome. Thus, the invention may be used to diagnose and screen for affective disorders, in particular unipolar depressive illness, and related anxiety disorders (for example panic disorder, obsessional compulsive disorder), migraine and irritable bowel syndrome.

The invention may also be useful in diagnosis of, or in identifying propensity to dementia such as alzheimer's disease, and to aggression, particularly that associated with dementia, since it can be shown that defective serotonin transmission in brain is linked to these abnormalities.

Migraine is one of the most common neurological disorders, affecting 16–23% of the general population (Rasmussen B K et al Cephalagia 1992;12:221–28, and Russell M B et al Int. J. Epidemiology 1995;24:612–18). There are two main types of migraine. The first, migraine without aura (MO; previously called common migraine) is characterised by headache attacks lasting 4–72 h. The headache is usually severe, unilateral, pulsating, aggravated by physical activity, and accompanied by nausea, vomiting, photophobia, and phonophobia. In the second type, migraine with aura (MA; previously classical migraine), the attack is preceded by an aura i.e., reversible visual, sensory, motor and/or aphasic symptoms. The ensuing headache is very similar to that of MO (Rasmussen B K et al. Cephalagia 1996;16:239–245).

The results of most family studies of migraine that use segregation analysis have suggested that genetic factors account for a significant degree of the variance of MO and MA. Russell and colleagues (see Neurology, 1993, 43: 1369–73) have studied 121 individuals with MO and 72 individuals with MA in a Danish population, diagnosed according to IHS criteria and ascertained from the community using the Danish Central Person Registry. They reported that, compared with the general population, the first-degree relatives of individuals with MO had a three-fold increase of MO, while the first-degree relatives of individuals with MA had a two-fold increase both of MO and of MA. Compared with the general population, few spouses had either MO or MA. This strongly suggested that MO and MA are genetically determined although the study suffered from the lack of direct interview of relatives.

A later, though similar study conducted by Russell & Olesen (see BMJ, 1995, 311: 541–4) the first-degree relatives of individuals with migraine were interviewed. They found that the first-degree relatives of individuals with MO and 1.9 times the risk of MO and 1.4 times the risk of MA. First-degree relatives of individuals with MA had 3.8 times the risk of MA and no increased risk of MO. The first-degree relatives of screened controls had no increased risk of MO or MA. Although a different pattern of results emerged from those reported in the 1993 study (see Russell et al 1993 supra), the results nevertheless strongly suggest that MO and MA have a different aetiology, and as they are based upon direct neurological interview and examination of all the relatives, are probably more reliable than the original study. The genes contributing to genetic susceptibility for MO and MA remain to be identified.

Mochi and colleagues (see Cephalagia, 1993, 13: 389–94) have performed segregation analysis on groups of families with MO and MA. The resulting heritability coefficients, a measure of the degree of concordance among first-degree relatives, indicate a major genetic component in both MO and MA, and were interpreted as suggesting for MA, a possible multifactorial threshold character, and for MO, the likely presence of a major susceptibility gene with reduced penetrance.

A greater understanding of molecular migraine mechanisms has come from the study of serotonin (5-HT) and its receptor subtypes. One of the most important initial strands of evidence implicating serotonin in the pathogenesis of migraine was the claim that its intravenous injection tends to reverse migrainous headache. Further work in this field has shown that during a migraine attack, platelet serotonin levels decrease, urinary serotonin increases in some patients, and 5-HIAA, a major metabolite of serotonin, may increase. Other evidence suggesting a role for serotonin is based on the observation that headache can be precipitated by reserpine (which depletes neural serotonin stores). In addition, it may be relieved by selective $5-HT_{1D}$ agonists such as sumatriptan, and blocked by treatment with methysergide (a serotonin receptor antagonist).

There is striking similarity between the epidemiology of migraine and that of depression, both disorders in which serotonergic mechanisms have been implicated. Major depression, like migraine, is a common disorder with estimated lifetime prevalence ranging from 2–12% for men and 5–25% for women, and it may be precipitated by reserpine in susceptible subjects. In addition, low levels of platelet serotonin and other abnormalities of its metabolites have been shown. Both migraine and depression show an efficacious response to treatment by tricyclic and monoamine oxidase inhibiting antidepressants, both having serotonergic activity.

Several studies have attempted to examine the association between migraine and depression. A clinical study by Merikangas and colleagues (see Psychiatry Res, 1988, 2:119–29) yielded significant associations between the two conditions. Systematic studies of migraine and depression in community samples have shown remarkable similarity in their reported results (see Merikangas et al, 1988 supra; Merikangas et al, Arch Gen Psychiatry, 1990, 47:849–53; and Breslau et al, Psychiatry Res, 1991, 37:11–23). The odds ratio (OR), which measures the degree of association between the two disorders, was nearly identical in these three studies (OR=3.5, 3.1, 3.6 respectively), confirming the clinical observation regarding an association between migraine and depression. Such co-morbidity may represent shared risk or common aetiology, a possibility also suggested by segregation analyses (see Merikangas et al, 1990, supra). It is plausible, therefore, that serotonin provides a common neurochemical basis for this interaction.

In more detail the number of VNTR repeats occurring in intron 2 of the serotonin transporter gene may be determined in vitro from a sample taken from the patient using technologies such as (for example) polymerise chain reaction (PCR), heteroduplex analysis and Southern blotting. Other methods include comparative genome hybridisation (Methods in Enzymology Rayburn, 1993, Vol 224, pages 204–212), single strand conformational polymorphism analysis (see Lenk et al, Neuromuscular Disorders 1994 4:411–418) and Ligase Chain Reaction (see Jou et al, J Human Mutation 1995 5:86–93). Where a probe is required in these techniques any sequence able to hybridise to the sequences of interest may of course be used.

In a preferred aspect the present invention provides methods of diagnosis and/or screening for psychiatric disorders or for susceptibility to migraine, which method comprises obtaining a sample from the individual and screening the sample in vitro to look for the number of VNTR repeats appearing in intron 2 of the serotonin transporter gene. Where 9 repeats of the VNTR are located it may be concluded that the individual can be considered to be at risk of or suffering from psychiatric disorders and the individual may be treated accordingly. Where 12 repeats of the VNTR are located it may be concluded that the individual can be considered to be at risk of or suffering from MO, whilst 9 repeats of the VNTR suggests an increased risk of MA. The present invention may be particularly of importance in aiding accurate prescription needs, especially having regard to the need for continuing therapy.

It may be convenient to conduct the methods of the present invention on DNA extracted from a blood sample, especially white blood cells. Any other physiological sample may also be suitable; mention may be made of body fluids containing DNA (such as saliva or blood) and other non-fluid samples such as hair.

The present invention will now be illustrated with reference to the following, non-limiting, examples.

FIG. 1 represents a comparison of the Lesch 10 prior art sequence and STin2.9 (SEQ ID NO 1), STin2.10 (SEQ ID NO 2) and STin2.12 (SEQ ID NO 3) of the present invention.

Figure 3:
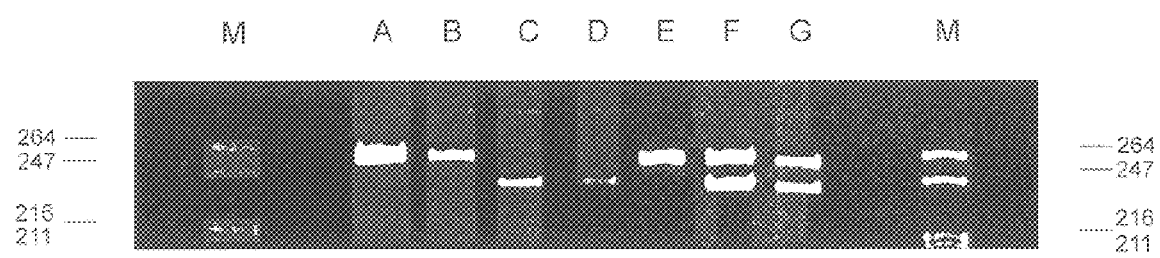

FIG. 3 shows an ethidium bromide stained 5% polyacrylamide gel showing PCR fragments from 7 DNA samples with 10+10 (A & E), 10+12 (B), 9+12 (C & D) and 9+10 (F & G) copies of 16 or 17 bp VNTR repeats. M=DNA markers.

Figure 4:
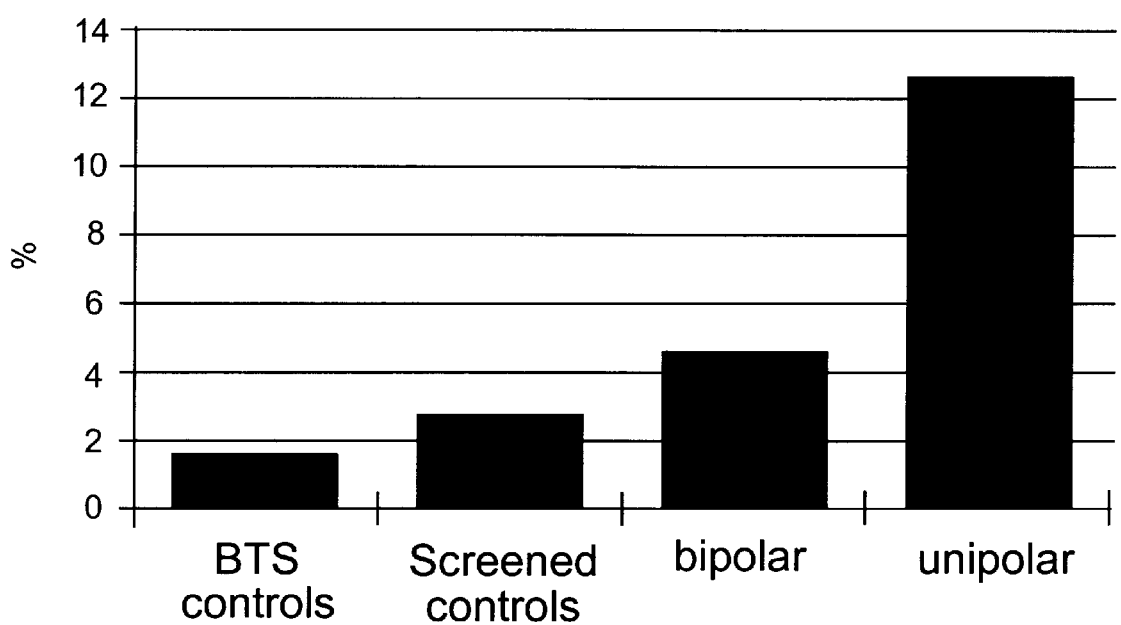

FIG. 4 represents the frequency of the STin2.9 allele in control, screened control, bipolar and unipolar groups of Example 1.

Figure 5:
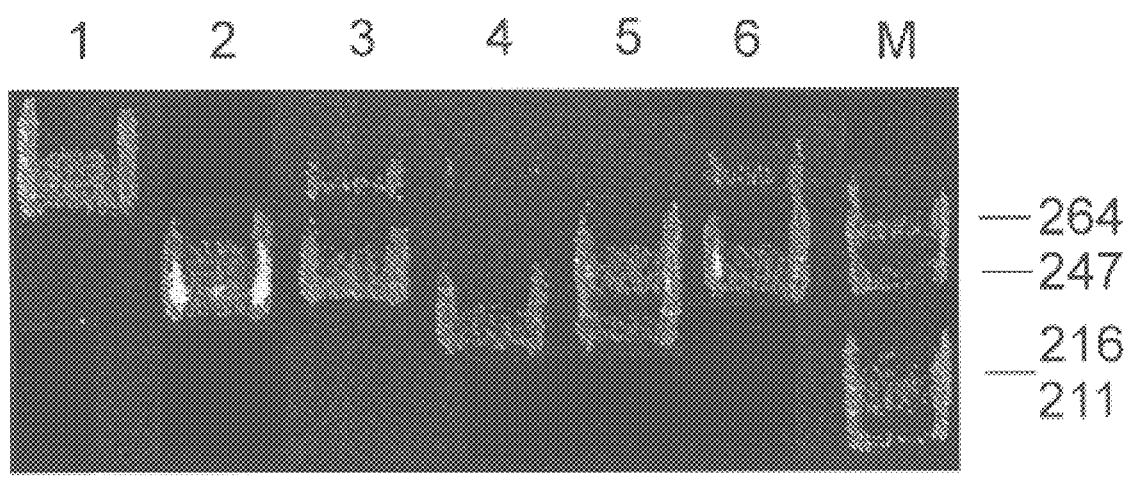

FIG. 5 shows an ethidium bromide stained 5% polyacrylamide gel showing PCR analysis of HSERT intron 2 in 6 individuals (Nos 1 to 6). M=DNA markers.

Figure 6:
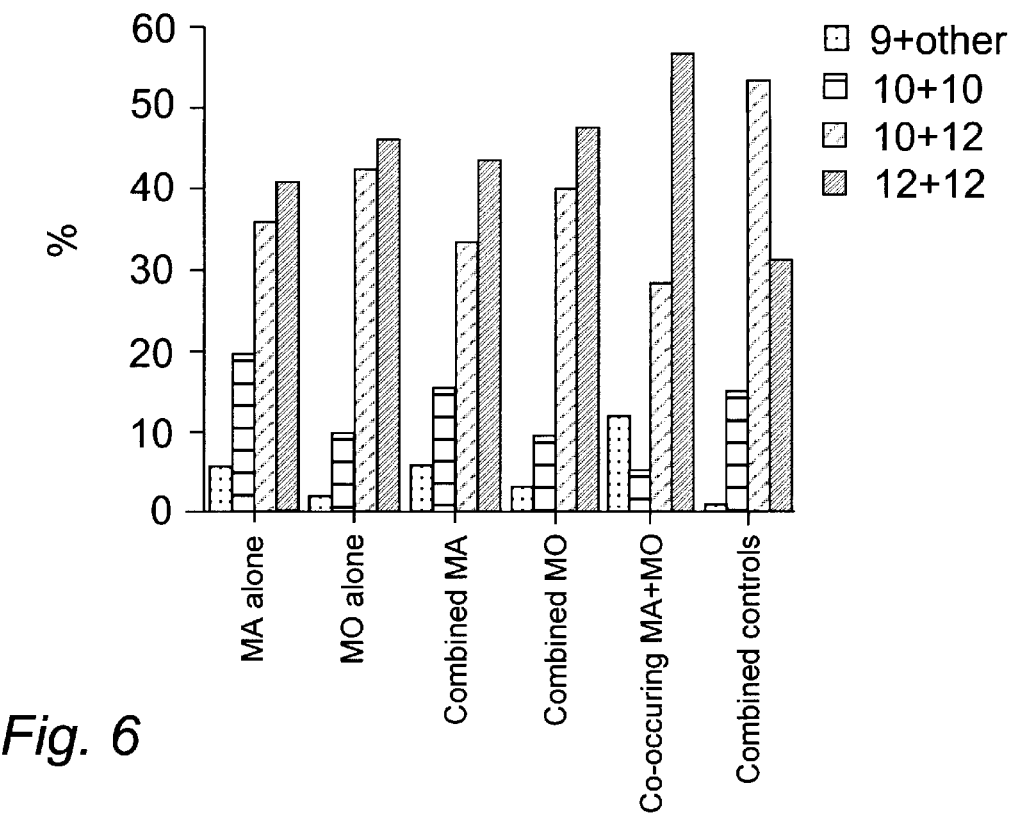

FIG. 6 shows the distribution of genotype frequency for VNTR in control and patient groups.

Figure 7:
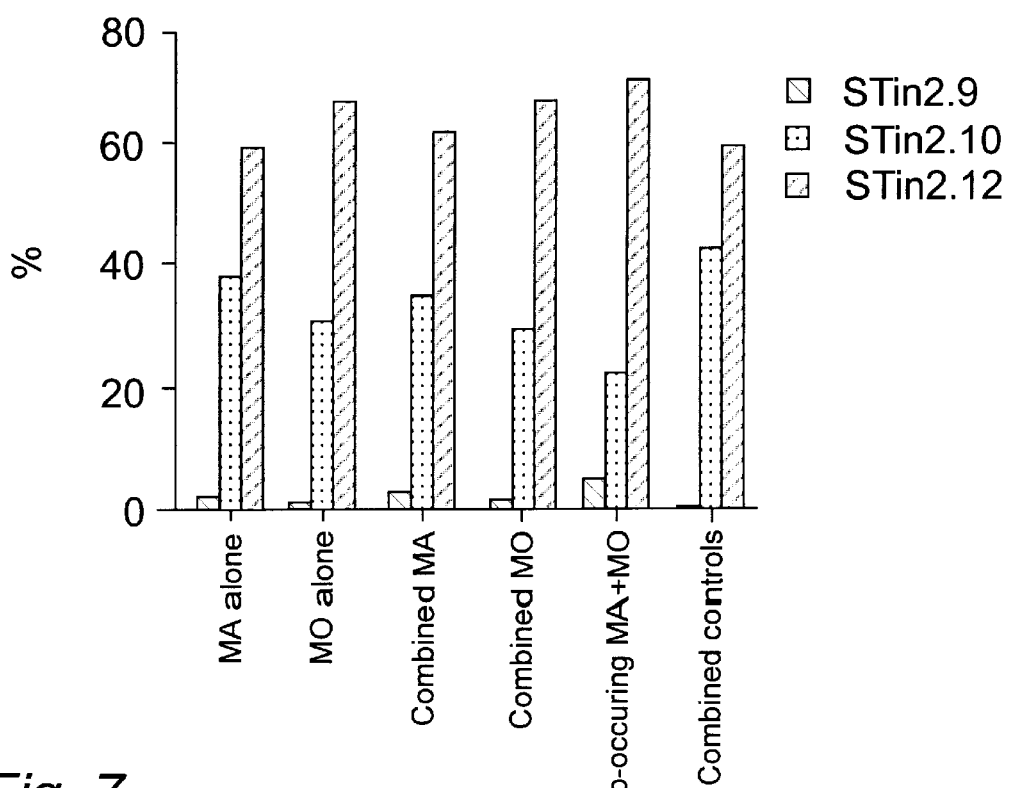

FIG. 7 shows the distribution of allele frequency for VNTR in control and patient groups.

EXAMPLE 1

Subjects and Methods. The design of the study was approved by the relevant Ethics Committee. Patients with major affective disorder were recruited from the inpatient and outpatient services of the Royal Edinburgh Hospital. We planned to enter at least 80 patients and 160 controls into the study. 39 patients with single or recurrent major depressive episodes and 44 patients with bipolar disorder were eventually included. All fulfilled both the DSM IV criteria (see American Psychiatric Association "Diagnosis and Statistical Manual of Mental Disorders" 3rd edition, revised, Washington DC, 1987) for major depressive disorder or bipolar disorder and also the "probable" Research Diagnostic Criteria (see Spitzer et al, Arch Gen Psychiatry 1978 35:773–782) according to the Schedule for Affective Disorders and Schizophrenia (Lifetime version)(SADS-L) (Endicott et al, Arch Gen Psychiatry 1978, 35:837–844) on interview and case note evaluation by an experienced psychiatrist.

Controls came from two sources. A group of 122 anonymous control samples were obtained through the co-operation of the local Blood Transfusion Service. They were not screened for the presence of a personal or family history of psychiatric disorder but met the normal criteria for blood donation and so were taking no regular psychotropic medication. A further group of 71 volunteer controls were obtained from several sources and was screened using a short questionnaire based on sections of SADS-L to exclude affective disorder, anxiety disorders other psychotic disorders and alcohol problems both in the subjects themselves and in first or second degree relatives. In addition, all those who suffered from probable migraine or irritable bowel syndrome, considered by some to be "affective spectrum disorders" in which a serotonergic mechanism has been implicated (see Hudson et al, Am J Psychiatry 1990 147:552–564) were excluded.

The mean ages of the patient and control groups were: unipolar 43.4, bipolar 43.7, screened controls 47.2. The sex ratios (female:male) were: unipolar (48.7:51.3), bipolar (47.0:53.0) and screened controls (35.2:64.8).

DNA Isolation. Venous blood samples were frozen immediately in dry ice and stored at −70° C. Genomic DNA was isolated as described previously (see Smith et al, Lancet 1992 339:1375–1377). Briefly, 100 μl of whole blood was washed three times in TE buffer (10 mM Tris-HCl, pH8, 1 mM EDTA), peripheral blood leucocytes were harvested by centrifugation and re-suspended in 100 μl lysis buffer (50 mM KCl, 20 mM Tris-HCl (pH 8.3), 2.5 mM $MgCl_2$, 0.45% Nonidet P-40, 0.45% Tween 20) containing 200 μg $ml^{-1}$ Proteinase K. Lysis was completed by incubation for 20 minutes at 55° C. and the crude lysates were diluted with an equal volume of sterile distilled water and heated to 96° C. for 10 minutes to inactivate the proteinase. Samples were either used immediately or stored at −20° C. until required.

Figure 2:
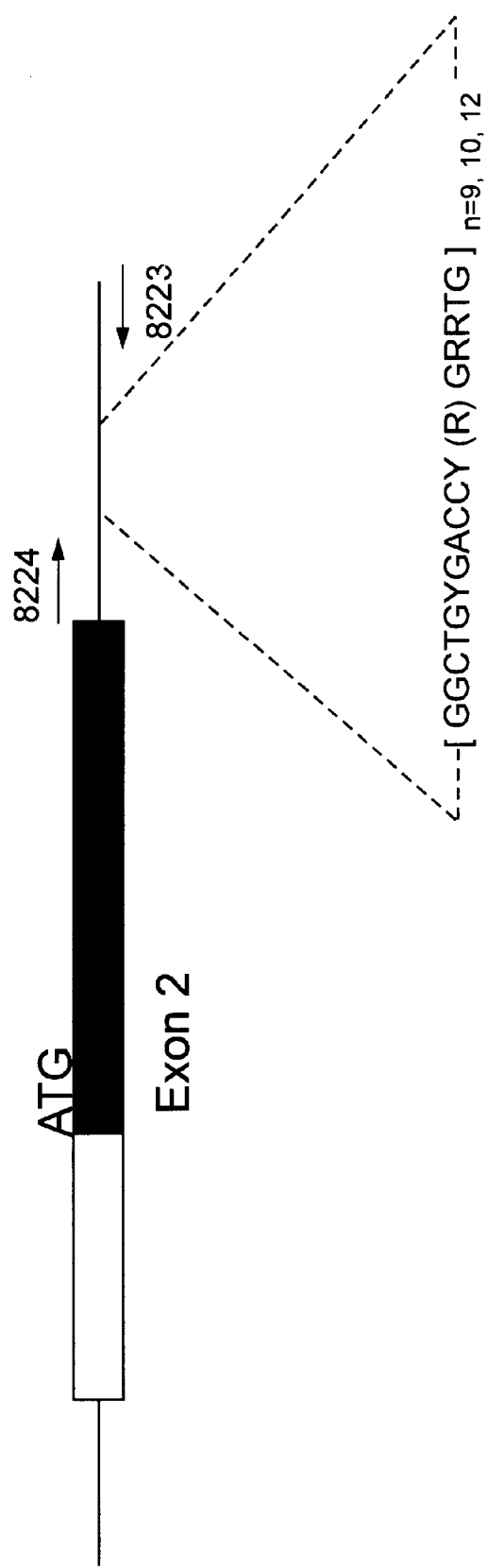
FIG. 2 is a schematic representation of the VNTR region of intron 2 of the serotonin transporter gene.

PCR of Intron 2. Target DNA (2–5 μl of lysate) was amplified by polymerase chain reaction using specific oligonucleotide primers; 8224 (5'GTCAGTATCACAGGCTGCGAG) and 8223 (5'-TGTTCCTAGTCTTACGCCAGTG) whose sequences appear in the sequence listing at SEQ ID Nos: 5 and 4 respectively. This primer pair amplifies the VNTR region of intron 2 containing the 17 bp repetitive element as is illustrated in FIG. 2. PCR was carried out using 1.5 U Taq polymerase (Promega), 100 ng of each primer, 200 μM each of dATP, dCTP, dGTP, and dTTP, 0.5% or 1.0% (v/v) DMSO and 1.5 mM $MgCl_2$ in 1×PCR buffer (Promega) (50 mM KCl, 10 mM Tris-HCl (pH9), 0.1% Triton X-100) in a final reaction volume of 50 μl. Thermal cycling was carried out in a Hybaid Omnigene with a PCR profile starting with an initial strand separation at 94° C. for 4 minutes followed by 35–43 cycles of primer annealing at 60° C. (20 s), polymerisation at 72° C. (20 s) and denaturation at 94° C. (30 s). A final polymerisation step of 120 s was carried out to complete elongation of all amplified strands. Amplified fragments were resolved on 5% non-denaturing polyacrylamide gels and bands visualised by ethidium bromide staining and UV transillumination (FIG. 3). The identity of the products was confirmed by digestion with restriction enzymes HaeIII, BstN I and Sma I and by direct sequencing.

Amplified fragments were separated on 2% agarose gels, excised and purified by the Wizard PCR DNA purification system (Promega). Sequencing was performed using the Prism DyeDeoxy Terminator Cycle sequencing kit with one of the primers used to generate the PCR product. The sequencing reactions were performed in a Perkin Elmer Cetus thermal cycler (30 cycles consisting of 30 s at 96° C., 15 s at 50° C. and 4 min at 60° C.). Unincorporated nucleotides were removed by phenol/chloroform extraction. Electrophoresis was carried out on an Applied Biosystems model 373 STRETCH DNA Sequencer at a constant power of 30 W for 12 hours using a 4.75% denaturing polyacrylamide gel.

Statistical Analysis. Patients were examined both as separate unipolar and bipolar disorder groups and as a combined group. Analysis was carried out on the raw frequencies by the Chi squared test and by the Fisher exact test (two tailed). These calculations were performed using the Statistical Package for the Social Sciences (Apple Mackintosh version 4.0). In addition odds ratios and confidence limits were calculated by standard methods.

Heteroduplex Analysis. PCR products were denatured for 3 minutes at 95° C. and allowed to cool to 37° C. over 30 minutes. Samples (5 µl) were electrophoresed through MDE Hydrolink gels (AT Biochem) at 800 V overnight and bands were visualised by silver staining.

Results.

Three alleles of the VNTR region in intron 2 of the serotonin transporter gene were detected by PCR followed by polyacrylamide gel electrophoresis. The sequence data for the three alleles is presented in FIG. 1. By sequencing representative PCR products, we identified three novel alleles (STin2.9, STin2.10 and STin2.12) containing, respectively, 9, 10 and 12 copies of the VNTR repeat. The third allele present in our subjects (STin2.10) contained 10 copies of the repeat and differed from that as described by Lesch et al 1994, supra). We were unable to identify any individuals possessing 11 copies of the repeat.

All chromosomes examined contained either 9, 10 or 12 copies of the 17 bp repeat, with frequencies of 0.02, 0.40 and 0.58 respectively. The consensus sequence is:

GGCTGYGACCY(R)GRRTG

There was loss of the 12th base in 3 repeats. STin2.12 showed an additional 2 repeats in the area of alternating 16 and 17 bp motifs. 11 copies of the VNTR were not seen in any of the PCR products analyzed here. The third novel allele on the VNTR containing 9 copies of the repeat is identical to STin2.10 except for the loss of the 6th repeat.

There are some minor differences between some of the repeats within the consensus sequence and the pattern of repeats for the various alleles may be represented as follows (see FIG. 1):

| | | | | | | | | | | | |
|---|---|---|---|---|---|---|---|---|---|---|---|
| STin2.12 | A | B | C | D | E | F | D | G | D | G D | F |
| STin2.10 | A | B | C | D | E | F | | | D | G D | F |
| STin2.9 | A | B | C | D | E | | | | D | G D | F |
| Lesch | A* | B | C | D* | E | G | D* | | G | D* | F |

*indicates that the repeat does not correspond exactly to that of the novel repeats in the present invention.

It is interesting to note that in STin2.9 the 6th repeat is a 16 mer rather than a 17 mer as in the other two alleles of the present invention.

Since there was no significant difference in the frequency of the three alleles between the screened and BTS control groups, all further statistical comparisons were made between the patient groups and the combined control group.

There was a significantly higher frequency of genotypes containing the STin2.9 allele in the unipolar group compared to the control group (P<0.002: Table 1, and FIG. 4). There was also a statistically significant difference between the combined affective disorder group and the control group in the frequency of individuals carrying the STin2.9 allele (P<0.02:Table 1). These differences were significant in a two-tailed Fisher's exact test at P<0.01 and P<0.05, respectively. When allele frequencies were considered, there remained a significant difference between the unipolar and control groups ($\chi^2$=9.87, P<0.01: Table 1). In addition there appeared to be a tendency for affected individuals to have allelic forms with fewer VNTRs than control subjects ($\chi^2$= 9.56, P<0.05).

Odds ratios were calculated for the risk of affective disorder if a single copy of the STin2.9 allele was present. For the risk of unipolar disorder given a single STin2.9 allele, the odds ratio was 6.95, with 95% confidence limits of 1.8–27.2 (Table 1).

Discussion

A dysfunction or the serotonergic system has long been suspected in depression and other affective and anxiety disorders but could not previously be definitely linked to any defect thereof. Drug-free depressed patients have been reported to have reduced serotonin metabolites in CSF and postmortem brain tissue, decreased plasma tryptophan concentrations and an increase in the density of brain 5-HT$_2$ binding sites (see Ins et al, Clin Chem 1994, 40:288–295).

It is known that antidepressant drugs which act specifically to block serotonin re-uptake have comparable efficacy to tricyclic antidepressants and monoamine-oxidase inhibitors which act on other monoamine neurotransmitters as well as serotonin. Many investigators have reported low numbers of platelet and brain serotonin (5-HT) transporter sites in drug-free depressed patients (see Boyer et al, "Selective serotonin re-uptake inhibitors, Chichester: John Wiley & Sons Ltd, 1991, pages 71–80 and references cited therein). Our results suggest a mechanism by which genetic variability in the serotonin transporter gene may play a role in determining in susceptibility to depression.

There are now several documented examples of neuropsychiatric disorders caused by variations of expansion of triplet repeats (see Ross et al, Trends Neurosci 1993, 7:254–260) but few instances in which VNTRs with longer repeating sequences confer susceptibility to disease. The IDDM2 locus, conferring susceptibility to type 1 diabetes, has been mapped to a 14–15 bp VNTR located between the tyrosine hydroxylase and insulin genes on chromosome 11p15.5 (see Bennett et al, Nature Genet 1995, 9:284–292). A VNTR with a 40 bp repeating sequence in the dopamine transporter gene, which is closely related to the serotonin transporter gene, has been suggested to play a role in determining susceptibility to some forms of alcoholism (see Perisco et al, Biol Psychiatry 1993, 34:265–267 and Goldman Nature Med 1995, 1:624–625).

There are several possible mechanisms by which variation in the VNTR in the serotonin transporter gene might influence susceptibility to affective disorders. Variations in the VNTR region may play a role in regulation transcription, possibly through an adjacent AP-1 motif (see Lesch et al, 1994, supra). Variations in the VNTR at the IDDM2 locus have been shown to influence the expression of insulin mRNA in pancreatic cell lines: gene constructs containing haplotypes of the VNTR which confer susceptibility to type 1 diabetes are expressed at higher levels than other haplotypes (see Lucassen et al, Hum Mol Genet 1995, 4:501–506). Alternatively, the polymorphism may be in linkage disequilibrium with a susceptibility locus nearby, as is the case for alleles of a VNTR downstream of the human phenylalanine hydroxylase gene (see Goltsov et al, Am J Human Genetics 1992 51:627–636).

EXAMPLE 2

The preliminary study described in Example 1 was expanded.

Subjects. The design of the expanded study was approved by the relevant committee for Medical Ethics.

One hundred and nineteen individuals with single or recurrent major depressive episodes and 128 individuals with bipolar disorder were compared with a group of 346 controls. These totals include 39 unipolar, 44 bipolar and 193 controls from our preliminary study (described in Example 1). Patients with major affective disorder were recruited from the in-patient and out-patient population of the Royal Edinburgh Hospital. All patients met DSM III-R criteria for major depressive disorder or bipolar disorder and also the probable Research Diagnostic Criteria according to the Schedule for Affective Disorders and Schizophrenia (Lifetime version) (SADS-LA) (Endicott and Spitzer 1978, Archives of General Psychiatry 35:837–844). Control samples were obtained from two sources: 103 volunteers who were screened to exclude past psychiatric illness by a brief interview and 243 anonymous donors from the Scottish Blood Transfusion Service who met usual criteria for blood donation and were therefore not currently on any psychotropic medication.

The methodology was as described above for Example 1, and a minimum of 15 examples of each allele were directly sequenced.

Statistical Methods. In addition to the Chi squared test and Fisher exact test (two tailed), a comparison of allele frequency distributions between the control and patient groups was made by multiple analysis of variance (MANOVA) using the Statistical Package for the Social Sciences (SPSS Apple Macintosh v 4.0). Bonferroni correction was applied to allow for multiple comparisons when the Chi squared test was employed to compare the affective sub-groups with controls. Odds ratios and confidence limits were calculated by standard methods.

Characterisation of the VNTR alleles supported the results reported in Example 1. The 15 examples of each allele sequenced proved to be identical and supported the consensus sequence and sequence of repeats reported in Example 1.

Association Study. Table 2 illustrates the distribution of genotypes and allele frequencies for the VNTR in the control and patient samples. The distributions of genotype and allele frequencies were similar in the total control and patient samples compared to those described for the preliminary study.

There was a significant difference between patients with affective disorder and controls in the proportion of individuals carrying the STin2.9 allele (Table 2). This was true for both unipolar and bipolar sub-groups although there appeared to be a larger effect in the unipolar group (Table 2). For the risk of unipolar disorder given a single STin2.9 allele, the odds ratio was 4.44 (95% Cl, 1.65–11.95) and for bipolar disorder 3.22 (95% Cl, 1.15–909).

The mean age of the volunteer controls was 45.04 (SD 15.21) and of the patients 41.23 (SD 15.00). There was no significant sex difference in the distribution of STin2.9 allele between patient and control groups ($\chi^2$=0.99).

Allele frequencies were also calculated for the control and patient groups (Table 2). MANOVA showed a significant difference in overall allele distribution between the affective disorder group v control group and the unipolar v control group (Table 2). There was a similar trend in the bipolar sample which did not reach statistical significance (p=0.065, 2 d.f., two tailed).

Discussion.

There was a significant overall difference between affective disorder and control groups in the frequency distribution of alleles of the human serotonin transporter gene. The main finding is a significant increase in the frequency of the STin2.9 allele in patients with major affective disorder. This extends the previous finding described in Example 1 to a larger patient and control samples from the same population.

The structure of the VNTR consisted of 9, 10 or 12 copies of a 16–17 bp motif. The three alleles contained seven variants of the repetitive element (indicated as A–G in FIG. 1) in a specific order. We did not detect any allele containing 11 repeats, even though it has been reported in another study that the majority of chromosomes examined contained either 10 or 11 copies (Lesch et al, 1994, Journal of Neural Transmission 95:157–162). STin2.10 is similar to the 10 repeat allele described by Lesch et al, 1994 supra although repeats A and D show slight sequence variation and the order of elements seen here is ABCDEFDEDF rather than ABCDEEDEDF.

Comparison of the STin2.9, 10 and 12 alleles suggests that the shorter forms may have been generated by loss of central repeating elements. Evidence from VNTRs such as those in the collagen type II (COL2A1) and Apolipoprotein B genes suggest that the secondary DNA structure may be important in the generation of new alleles (Berg and Olaisen, 1993, Genomics 16:350–354; Desmarais et al, 1993, Nucleic Acids Research 21: 2179–2184). The sequences of VNTRs may favour the formation of hairpins and loops, which could result in the formation of new alleles by replication slippage.

The particular association between the occurrence of a STin2.9 allele and the risk of affective disorder requires explanation. The level of serotonin transporter gene transcription may be influenced by the sequences of the repetitive elements. VNTRs close to the insulin (IDDM2 locus) and HRAS1 genes bind transcription factors and show allelic variation associated with disease (Catignani Kennedy et al, 1995, Nature Genetics 9:293–298; Green and Krontiris, 1993, Genonics 17:429–434). These VNTRs regulate transcription in a cell and promoter specific way and small differences in nucleotide sequence influence the level of transcriptional activity. At the IDDM2 locus, the absence of a single 14 bp repeat element designated "e" has been suggested to cause loss of a protective effect against the development of insulin dependent diabetes (Bennett et al, 1995, Nature Genetics 9:284–292). By analogy, the absence of the 16 bp element "F" near the centre of the VNTR may also have functional consequences. Alternatively it may simply be the overall length of the VNTR which is adjacent to a putative transcription factor (AP-1) binding site, that is important.

These findings support that hypothesis that allelic variation in the serotonin transporter gene may contribute to susceptibility for both major depression and bipolar disorder.

EXAMPLE 3

This example investigates the role of allelic variation in the human serotonin transporter gene (HSERT), and in particular the variable number tandem repeat (VNTR) polymorphism in the second intron of the gene in individuals with MO, MA, MO+MA and unaffected controls.

Subjects and Methods. Subjects were obtained by screening all 40 year olds drawn from the population in a region outside Copenhagen using the Danish Central Person Registry, in collaboration with Russell and colleagues. This sample represents a unique group of migrainous individuals from what is effectively an epidemiological catchment area. Seventy-six individuals with MA alone and 92 with MO alone were included. Eighteen individuals with co-occurrence of both MO and MA were also included (see Russell et al, 1988, supra). For later analysis, this co-occurrence group was treated both independently and as part of the "combined MA" and "combined MO" groups. Forty-eight controls drawn from the Danish population who had been screened by a neurologist to rule out any personal history of migraine were included. In addition a group of 103 Scottish volunteer controls who had been screened by questionnaire to exclude a personal history of migraine were also included.

Methods

DNA Extraction and Polymerase Chain Reaction Analysis

Venous blood samples were obtained from the study sample in EDTA vials, and were frozen immediately. They were stored at −80° C. prior to DNA isolation. Genomic DNA was isolated as described by Smith et al (see The Lancet, 1992, 339:1357–7). Briefly the procedure was as follows:

DNA Isolation: 100 µl venous blood was placed in a microcentrifuge tube and washed in 750 µl TE buffer by thorough mixing and centrifuging at 14,000 g for 2 minutes. The supernatant was aspirated, and the pellet washed a further two times with 500 µl TE to complete lysis of red blood cells. The final pellet (peripheral blood leucocytes) was lysed by adding 100 µl lysis buffer containing 200 µg/ml Proteinase K. After incubation at 55° C. for 20 minutes, 100 µl of sterile water was added to the crude lysate, and this was heated to 98° C. for 10 minutes to inactivate the proteinase.

Polymerase Chain Reaction Analysis. Target DNA was amplified by the polymerase chain reaction (PCR) using the specific oligonucleotide primers 8224 (5'-GTCAGTATCACAGGCTGCGAG-3') and 8223 (5'-TGTTCCTAGTCTTACGCCAGTG-3'), according to standard protocols (Ogilvie et al. Lancet 1996;347:731–733). Each 50 µl PCR amplification reaction contained 3 µl DNA lysate, 1.5 mM $MgCl_2$, 4.5 µl 10× reaction buffer, 1% (v/v) DMS0, 200 µM each dNTP, 200 ng each primer and 1.5 U Taq DNA polymerase. Forty-five cycles (30 s of denaturation at 94° C., 30 s of primer annealing at 60° C., 30 s of polymerisation at 72° C.) were performed using a Hybaid Omnigene thermocycler, with initial strand separation carried out at 94° C. for 5 minutes. A final polymerisation step of 1 minute was performed to complete elongation of all amplified strands.

Amplified products were separated on 2% agarose gels, excised and purified by the Wizard PCR DNA Purification System. Sequencing was achieved using the ABI PRISM Dye Terminator Cycle Sequencing Ready Reaction Kit with AmpliTaq DNA Polymerase, FS in a Perkin Elmer Cetrus thermocycler (30 cycles of 30 s at 96° C., 15 s at 50° C., 4 min at 60° C.) with reverse primer 8223. Extension products were purified by ethanol precipitation. Electrophoresis was performed on a 4.75% acrylamide and urea gel run for 13 hours at a constant power of 30 W, using a model 373A STRETCH DNA Sequencer. Samples were stored at −20° C. until required.

Target DNA was amplified by the polymerase chain reaction (PCR) using the specification oligonucleotide primers 8224 (5'-GTCAGTATCACAGGCTGCGAG-3') and 8223 (5'TGTTCCTAGTCTTACGCCAGTG-3'), according to standard protocols (see Smith et al, 1992, supra). The primer pair amplifies the region of intron 2 containing the 16–17 bp repetitive element (FIG. 2). To distinguish between alleles, fragments were separated by electrophoresis through a 5% non-denaturing polyacrylamide gel, and bands visualised by UV transillumination of gels stained with ethidium bromide (FIG. 5).

FIG. 5 shows PCR analysis of HSERT intron 2 in 6 individuals. 5% Polyacrylamide gel stained with ethidium bromide is shown. Five different genotypes can be identified: STin2.12/STin2.12 (300 bp: lane 1); STin2.10/STin2.10 (267 bp: lane 2); STin2.10/STin2.12 (267 bp+300 bp: lanes 3 and 6); STin2.9/STin2.12 (250 bp+300 bp: lane 4); and STin2.9/STin2.10 (250 bp+267 bp: lane 5). M indicates the lane containing DNA markers of the molecular sizes indicated.

Examples of each allele in each of the study groups were directly sequenced as described above. Alleles were identified and sequences constructed using GeneJocky II.

Statistical analysis. Comparison of allele frequency distributions between the control and patient groups and analysis of genotype distribution was carried out on the raw frequencies by the $\chi^2$ test. Yate's continuity correction was applied for any 2 by 2 tables with cells having values less than 10. Overall allele frequency distributions were compared between the control and patient groups by multiple analysis of variance (MANOVA). The Statistical Package for the Social Sciences was used (SPSS Mac v4.0). Hardy-Weinberg equilibrium of observed allele frequencies was examined by $\chi^2$ analysis.

RESULTS

Characterisation of the VNTR Alleles. Three alleles of the intron 2 VNTR region of human serotonin transporter (HSERT) were identified in the Danish individuals (FIG. 5). All of the suspected STin2.9 alleles (nine in total), plus six examples of each of the alleles corresponding to STin2.10 and STin2.12 were sequenced and proved to be identical to those described in Example 1 with no differences between groups. The three alleles contained respectively, 9(STin2.9), 10(STin2.10) and 12(Stin2.12) copies of a repetitive element present as seven variants (indicated as A to G in FIG. 1).

Association Study. The distribution of genotype and allele frequencies for the VNTR in control and patient groups is shown in Table 3a. FIGS. 6 and 7 show, respectively, the distribution of genotype frequency and allele frequency according to the group studied.

There was no significant difference in the overall distribution of genotypes between the Danish and the Scottish screened control groups ($\chi^2$=0.56 (3 df), p=0.0906). In view of this similarity, further comparisons with the patient groups were done using both the Danish controls on their own and a combined group including all 151 controls.

Comparing the MO group to the combined controls, there was significant increase in the frequency of individuals and the STin2.12/STin2.12 genotype ($\chi^2$=4.71 (1 df), p<0.05). In addition, MO patients showed a significant move away from having a single copy of the STin2.10 allele when compared with combined controls ($\chi^2$=4.07 (1 df), p<0.05), although clearly these findings may be interdependent. This effect was also significant in the "combined MO group", which showed a shift in allele frequency distribution from having a single copy of the STin2.10 allele ($\chi^2$=6.14 (1 df), p<0.02)to having two copies of the STin2.12 allele ($\chi^2$=4.80 (1 df), p<0.05). For the risk of MO given a homozygous STin2.12 genotype, the odds ratio was 2.177 (95% CI 1.053–4.501) compared to the Danish control group on its own. MANOVA showed a significant difference in the overall allele frequency distribution between the combined MO group versus combined controls (F=3.72 (2 df), p=0.026). This was reflected in the genotype distribution of the combined MO group where the frequency of STin2.10/STin2.12 individuals was reduced ($\chi^2$=4.75 (1 df), p<0.05) while the frequency of STin2.12/STin0.12 individuals was increased ($\chi^2$=6.46 (1 df), p<0.02).

The combined MA group had a significant increase in STin2.9 carriers ($\chi^2$=4.69 (1 df), p<0.05), and for the risk of MA given a single copy of STin2.9, the odds ratio was 5.080 (95% CI, 1.003–25.716). If patients with co-occurrence of both MO and MA were excluded, there remains a non-significant trend in this direction. The MA alone group showed a much lower frequency of STin2.10/STin2.12 individuals than combined controls ($\chi^2$=6.65 (1 df), p<0.01). There was also a significant decrease in individuals with the STin2.10/Stin2.12 genotype in both MA groups. However, MANOVA failed to show a significant difference in overall allele frequency distribution of either MA group.

The group with co-occurrence of both MO and MA showed a significantly different pattern of overall allele frequency distribution (F=5.34 (2 df), p=0.006), again with a reduction in STin2.10 carriers compared to the combined controls ($\chi^2$=4.34 (1 df), p<0.05) and this difference was also significant when compared to the Danish controls alone (Table 3a).

Table 3b shows a parallel study with an amplified population, where similar subjects were chosen from Danish MO and MA sufferers. 173 individuals having MO and 94 having MA were included. 18 individuals met criteria for both MO and MA. The control group of 133 individuals comprised 85 individuals from the same source as the subjects and 48 other volunteers from the Copenhagen area. All participants had a clinical interview and a physical and neurological examination by an experienced neurological resident. The operational diagnostic criteria of the International Headache Society (Society HCCotIH. Cephalagia 1988;Supplement 17:1–96) were used. The project was approved by the Danish Ethics Committee. Methods previously described were employed.

Results:

Comparing the MO group to controls, MO patients showed a significant move away from genotypes having a copy of the STin2.10 allele ($\chi^2$=5.70, (1 df), P=0.017) and a significant increase in the frequency of individuals with genotypes having a copy of the STin2.12 allele ($\chi^2$=4.68, (1 df), P=0.031) although the difference in the overall allele frequency distribution did not reach significance. In the MO group, 44.5% of individuals had a homozygous STin2.12 genotype compared to 32.3% of controls. For the risk of MO given a genotype homozygous for the STin2.12 allele, the odds ratio was 1.68 (95% CI, 1.05–2.69) compared to other genotypes.

The MA group also showed a non-significant trend away from carrying the STin2.10 allele ($\chi^2$=3.29, (1 df), P=0.07). This was associated both with non-significant increases in STin2.12 carriers ($\chi^2$=3.01, (1 df), P=0.083), and in STin2.9 carriers to 6.4% compared to 2.3% in the controls. This latter difference, when considered as the risk of MA given a single copy of STin2.9, was represented by an odds ratio of 2.95 (95% CI, 0.72–12.13). This increase in STin2.9 carriers in the MA group was in contrast to the MO group, where there was no suggestion of such a change ($\chi^2$=0.08, (1 df), P=0.779).

The group with co-occurrence of both MO and MA showed a significantly different pattern of overall allele frequency distribution from controls ($\chi^2$=7.39, (2 df), P=0.025), reflecting a significant reduction in genotypes containing the STin2.10 allele when compared to controls ($\chi^2$=3.95, (1 df), P=0.047), and a non-significant shift both to STin2.9 carriers(OR=5.42, 95% CI, 0.84–34.90) and to STin2.12 homozygosity(OR=2.62, 95% CI, 0.96–7.10)

Discussion

This example confirms by sequencing the existence in a non-British population of identical allelic forms of the human serotonin transporter gene intron 2 VNTR to those previously described. The example demonstrates a difference in the allelic distribution of the VNTR between individuals with co-occurence of MO and MA, and unaffected controls. In addition, an apparent dissociation between individuals suffering from migraine without aura and individuals suffering from migraine with aura in genotype distribution at this locus is demonstrated.

The data are suggestive that the STin2.10 allele may be protective against the development of both types of migraine. MO patients show a significant shift away from carrying the ten repeat, STin2.10 allele, towards having the STin2.12 allele. While the MA patients also show such a trend, they exhibit both a threefold increase in carriers of the rare STin2.9 allele as well as a move towards STin2.12 homozygozity when compared to controls. The findings regarding the group of individuals with co-occurrence of both MO and MA is intriguing. Such co-occurrence is rare and the group is therefore small in this epidemiological sample. However, the presence of a statistically significant separation in overall allele distribution in this group, when compared to controls, and a significant reduction in genotypes with a STin2.10 allele associated with both a trend to STin2.9 elevation and an increase in STin2.12 homozygosity, may reflect the contribution of the different alleles to each disorder while also reinforcing the distinctiveness of MO and MA.

MO patients show a significant shift towards the STin2.12 allele, while the MA patients show a move towards more STin2.9 carriers when compared to controls. The HSERT VNTR polymorphism may be only one of a number of genes which may mediate susceptibility to migraine. It is interesting to note that the segregation analysis performed by Mochi and colleagues suggested the involvement of two or more genes (see Mochi et al, 1993, supra), and their proposed reduced penetrance model may in fact be concealing a more complex pattern of inheritance. In light of the proposed role of allelic variation in the serotonin transporter gene as a susceptibility factor for major depression, it is of particular interest that MA has been shown to be the type of migraine most strongly associated with depression (Breslau et al supra). It is important to emphasise that patients were not excluded from either control or patient groups in the present study on the basis of a history of affective disorder and that this could be a confounding factor. Breslau and colleagues (see Breslau et al, 1991, supra) have shown that the odds ratio for migraine and depression co-morbidity is generally higher with MA versus controls (OR=4.0; 95% CI, 2.2–7.2) than with MO versus controls (OR=2.2; 95% CI, 1.2–4.0).

The findings regarding the group of individuals with co-occurrence of both MO and MA is intriguing. Such co-occurrence is rare and the group is therefore small in this epidemiological sample. However, the finding of both a trend to STin2.9 elevation and an increase in STin2.12 homozygosity in the presence of a statistically significant separation in overall allele distribution when compared to controls (F=5.34 (2 df), p=0.006), may reflect the contribution of the different alleles to each disorder while also reinforcing the distinctiveness of MO and MA.

The differences found in the observed and expected genotype distribution for the MA group may be explained by Russell's observation (see Cephalalgia, 1996) of a bimodal distribution in age at onset in MA patients with MA, suggesting the existence of two subtypes of MA. The failure of the combined patient and combined control groups to meet Hardy-Weinberg equilibrium may simply be due to the fact that they are an amalgamation of two separate groups.

These data support the view that susceptibility to MO and MA has a genetic component and that genetic susceptibility may in some cases be associated with a locus at or near the serotonin transporter gene. They also suggest that, in particular, the group of individuals with co-occurrence of MO and MA may be worthy of further investigation. The apparent dissociation between MO and MA with regard to patterns of HSERT genotype distribution is also of interest in light of the ongoing debate over whether MO and MA are in fact separate disorders or merely subtypes of a unitary entity. These data support the increasing epidemiological evidence suggestive of a true separation between the two disorders.

TABLE 1

Distribution of genotypes and allele frequencies of the VNTR in control and patient groups

| | | Genotype Distribution (%) | | | |
|---|---|---|---|---|---|
| | n | STin2.9/ other | STin2.10/ STin2.10 | STin2.12/ STin2.12 | STin2.10/ STin.12 |
| Combined Controls | 193 | 2.1 | 14.5 | 33.7 | 49.7 |
| BTS | 122 | 1.6 | 13.9 | 35.2 | 49.2 |
| Screened | 71 | 2.8 | 15.5 | 31.0 | 50.7 |
| Affective Disorder | 83 | 8.4[a] | 21.7 | 31.3 | 38.6 |
| Bipolar | 44 | 4.5 | 27.3 | 31.8 | 36.4 |
| Unipolar | 39 | 12.8[b] | 15.4 | 30.8 | 41.0 |

| | | Allele Frequency (%) | | |
|---|---|---|---|---|
| | n | STin2.9 | STin2.10 | STin2.12 |
| Combined Controls | 386 | 1.04 | 39.64 | 59.33 |
| BTS | 244 | 0.82 | 38.93 | 60.25 |
| Screened | 142 | 1.41 | 40.85 | 57.75 |
| Affective Disorder | 166 | 4.22[c] | 41.57 | 54.22 |
| Bipolar | 88 | 2.27 | 45.45 | 52.27 |
| Unipolar | 78 | 6.41[d] | 37.18 | 56.41 |

Statistically significant differences from the combined control group were as follows:
[a] $\chi^2 = 6.14$, $P < 0.02$. O.R. = 4.35, 95% C.I. 1.2–15.3. Survives Fisher exact test (two-tailed) at $P < 0.05$.
[b] $\chi^2 = 10.05$, $P < 0.002$. O.R. = 6.95, 95% C.I. 1.8–21.2. Survives Fisher exact test (two-tailed) at $P < 0.01$.
[c] $\chi^2 = 4.49$, $P < 0.05$. O.R. = 4.20, 95% C.I. 1.2–14.6.
[d] $\chi^2 = 6.00$, $P < 0.02$. O.R. = 6.51, 95% C.I. 1.7–24.9.

TABLE 2

Distribution of genotype and allele frequencies of VNTR in control and patient groups

| | N | 9 + 10 or 12 | Genotype distribution (%) | | | | | Allele Frequency (%) | | | F |
|---|---|---|---|---|---|---|---|---|---|---|---|
| | | | 9 10 | 9 12 | 10 10 | 10 12 | 12 12 | STin2.9 | STin2.10 | STin2.12 | |
| Controls | | | | | | | | | | | |
| All controls | 346 | 2.02 | 0.29 | 1.73 | 14.74 | 50.87 | 32.31 | 1.01 | 40.32 | 58.67 | |
| B.T.S. | 243 | 2.41 | 0.41 | 2.06 | 15.64 | 49.79 | 32.10 | 1.23 | 40.74 | 58.02 | |

TABLE 2-continued

Distribution of genotype and allele frequencies of VNTR in control and patient groups

| | | 9 + | Genotype distribution (%) | | | | | | Allele Frequency (%) | | | |
|---|---|---|---|---|---|---|---|---|---|---|---|---|
| | N | 10 or 12 | 9 10 | 9 12 | 10 10 | 10 12 | 12 12 | STin2.9 | STin2.10 | STin2.12 | | F |
| screened Patients | 103 | 0.91 | 0.00 | 0.97 | 12.62 | 53.40 | 33.01 | 0.49 | 39.32 | 60.19 | | |
| All affective disorder | 247 | 1.29[1] | 3.24 | 4.05 | 13.71 | 45.34 | 33.60 | 3.64 | 38.06 | 58.30 | | 5.08[4] |
| bipolar | 128 | 6.25[2] | 2.34 | 3.91 | 14.06 | 46.44 | 31.25 | 3.13 | 39.45 | 57.42 | | 2.74 |
| unipolar | 119 | 8.40[3] | 4.20 | 4.20 | 13.45 | 42.02 | 36.13 | 4.20 | 36.55 | 59.24 | | 5.42[5] |

Significant differences from the combined control group in the total sample:
[1] $\chi^2 = 9.89$, P = 0.0017, 1df;
[2] $\chi^2 = 5.45$, P = 0.0196, 1df;
[3] $\chi^2 = 10.23$ P = 0.0014, 1df;
[4] MANOVA, 2df, P = 0.006;
[5] MANOVA, 2df, P = 0.005.

TABLE 3a

Distribution of genotype and allele frequencies of VNTR in control and patient groups

| | | Genotype Distribution, % INI | | | | | | | Allele Frequency, % INI | | | |
|---|---|---|---|---|---|---|---|---|---|---|---|---|
| | N | 9 + other | 9 + 10 | 9 + 12 | 10 + 10 | 10 + 12 | 12 + 12 | N | STin2.9 | STin2.10 | STin2.12 | F |
| Controls | | | | | | | | | | | | |
| Combined | 151 | 1.32 [2] | 0.00 [0] | 1.32 [2] | 13.25 [20] | 53.64 [81] | 31.79 [48] | 302 | 0.66 [2] | 40.07 [121] | 59.27 [179] | |
| Scottish screened | 103 | 0.97 [1] | 0.00 [0] | 0.97 [1] | 12.62 [13] | 53.40 [55] | 33.01 [34] | 206 | 0.49 [1] | 39.32 [81] | 60.19 [124] | |
| Danish screened | 48 | 2.08 [1] | 0.00 [0] | 2.08 [1] | 14.58 [7] | 54.12 [26] | 29.17 [14] | 96 | 1.04 [1] | 41.67 [40] | 57.29 [55] | |
| Migraine with aura | | | | | | | | | | | | |
| Combined MA | 94 | 6.38 [6][1] | 4.26 [4] | 2.13 [2] | 15.96 [15] | 34.04 [32][2,A] | 43.62 [41] | 188 | 3.19 [6] | 35.11 [66] | 61.70 [116] | |
| alone | 76 | 5.26 [4] | 3.95 [3] | 1.32 [1] | 18.42 [14] | 35.53 [27][3,B] | 40.79 [31] | 152 | 2.63 [4] | 38.16 [58] | 59.21 [90] | |
| Migraine without aura | | | | | | | | | | | | |
| Combined MO | 110 | 3.64 [4] | 0.91 [1] | 2.73 [3] | 9.09 [10] | 40.00 [44][4] | 47.27 [52][5,C] | 220 | 1.82 [4] | 29.55 [65][7,D] | 68.84[151][10] | 3.72[11] |
| alone | 92 | 2.17 [2] | 0.00 [0] | 2.17 [2] | 9.78 [9] | 42.39 [39] | 45.65 [42][6] | 184 | 1.09 [2] | 30.98 [57][8] | 67.93 [125] | |
| Migraine with and without aura | | | | | | | | | | | | |
| MO + MA | 18 | 11.11 [2] | 5.56 [1] | 5.56 [1] | 5.56 [1] | 27.78 [5] | 55.56 [10] | 36 | 5.56 [2] | 22.22 [8][9,B] | 72.22 [26] | 5.34[12] |

Statistically significant differences from the combined control group were as follows:
[1] $\chi^2 = 4.69$, p < 0.05, 1df; OR = 5.000, 95% CI = 1.000–25.716
[2] $\chi^2 = 8.96$, p < 0.01, 1df; OR = 0.446, 95% CI = 0.262–0.760
[3] $\chi^2 = 6.65$, p < 0.01, 1df; OR = 0.476, 95% CI = 0.270–0.641
[4] $\chi^2 = 4.75$, p < 0.05, 1df; OR = 0.576, 95% CI = 0.350–0.948
[5] $\chi^2 = 6.46$, p < 0.02, 1df; OR = 1.924, 95% CI = 1.156–3.195
[6] $\chi^2 = 4.71$, p < 0.06, 1df; OR = 1.800, 95% CI = 1.056–3.076
[7] $\chi^2 = 6.14$, p < 0.02, 1df; OR = 0.627, 95% CI = 0.433–0.908
[8] $\chi^2 = 4.07$, p < 0.05, 1df; OR = 0.671, 95% CI = 0.455–0.990
[9] $\chi^2 = 4.34$, p < 0.05, 1df; OR = 0.427, 95% CI = 0.188–0.969
[10] $\chi^2 = 4.80$, p < 0.05, 1df; OR = 1.504, 95% CI = 1.043–2.168
[11] MANOVA, p = 0.026, 2df
[12] MANOVA, p = 0.006, 2df
Statistically significant differences from the Danish screened control group were as follows:
[A] $\chi^2 = 5.33$, p < 0.05, 1df; OR = 0.438, 95% CI = 0.215–0.888
[B] $\chi^2 = 4.18$, p < 0.05, 1df; OR = 0.466, 95% CI = 0.223–0.974
[C] $\chi^2 = 4.50$, p < 0.05, 1df; OR = 2.177, 95% CI = 1.053–4.501
[D] $\chi^2 = 4.43$, p < 0.05, 1df; OR = 0.587, 95% CI = 0.357–0.967
[E] $\chi^2 = 4.28$, p < 0.05, 1df; OR = 0.400, 95% CI = 0.615–0.969

TABLE 3b

Distribution of genotype and allele frequencies of VNTR in control and patient groups

| | | Genotype Distribution, % INI | | | | | | Allele Frequency, % INI | | |
|---|---|---|---|---|---|---|---|---|---|---|
| | N | 9 + 10 | 9 + 12 | 10 + 10 | 10 + 12 | 12 + 12 | N | STin2.9 | STin2.10 | STin2.12 |
| Controls | 133 | 0.8 [1] | 1.5 [2] | 14.3 [19] | 51.1 [68] | 32.3 [43] | 266 | 1.1[3] | 40.2 [107] | 58.7 [156] |
| Migraine without aura | 173 | 0.6 [1] | 2.9 [5] | 12.7 [22] | 39.3 [68][2] | 44.5 [77][4] | 346 | 1.7[6] | 32.7 [113] | 65.6 [227] |
| Migraine with aura | 94 | 4.3 [4] | 2.1 [2] | 16.0 [15] | 34.0 [32][3] | 43.6 [41] | 188 | 3.2[6] | 35.1 [66] | 61.7 [116] |
| Migraine with and without aura | 18 | 5.6 [1] | 5.6 [1] | 5.6 [1] | 27.8 [5] | 55.6 [10] | 36[1] | 5.6[2] | 22.2 [8] | 72.2 [26] |

Statistically significant differences from the control group were as follows:
[1] $\chi^2 = 7.39$, (2df), P = 0.025
[2] $\chi^2 = 4.26$, (1df), P = 0.039
[3] $\chi^2 = 6.52$, (1df), P = 0.011
[4] $\chi^2 = 4.68$, (1df), P = 0.031

What is claimed is:

1. A method of diagnosis of migraine or bipolar disorder or unipolar depression, or of susceptibility thereof in a human patient, said method comprising obtaining a sample of genetic material from said patient, analysing the number of copies of one or more alleles selected from the group consisting of STin2.9 (SEQ ID No. 1), Stin2.10 (SEQ ID No. 2) and Stin2.12 (SEQ ID No. 3) of the VNTR region in the second intron of the serotonin transporter gene present in said genetic material, wherein said number of copies indicates the likelihood of the patient suffering from migraine or bipolar disorder or unipolar depression.

2. A method as claimed in claim 1, wherein said method analyses the number of copies of one or more alleles selected from the group consisting of STin2.9 (SEQ ID NO 1), STin2.10 (SEQ ID NO 2) and STin2.12 (SEQ ID NO 3), and wherein the presence of STin2.9 (SEQ ID NO 1) indicates that the patient is at risk of or suffering from bipolar disorder or unipolar depression or MA migraine and wherein the presence of STin2.12 (SEQ ID NO 3) indicates that the patient is at risk of or suffering from MO migraine.

3. A method as claimed in claim 1 or claim 2 wherein the number of VNTR repeats or said alleles occurring in intron 2 of the serotonin transporter gene is determined in vitro.

4. A method as claimed in claims 1 or 2, wherein the number of VNTR repeats or the presence of said alleles is determined using one or more techniques selected from the group consisting of polymerase chain reaction, heteroduplex analysis, comparative genome hybridisation, single stand conformational polymorphism analysis, ligase chain reaction and Southern blotting.

5. A method as claimed in claim 1 or 2 wherein the sample comprises body tissue or body fluids containing DNA.

6. A method of diagnosis of migraine or bipolar disorder or unipolar depression or of susceptibility thereof by analysing the number of human VNTR repeats in the second intron of the serotonin transporter gene.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 150 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GGCTGTGACC CAGGGTGGGC TGTGACCCGG AGTGGGCTGT GACCCGGGGT GGGCTGTGAC      60

CCGGGTGGGC TGCGACCTGG GGTGGGCTGT GACCCGGGTG GGCTGTGACC TGGGGTGGGC     120

TGTGACCCGG GTGGGCTGTG ACCTGGGATG                                      150
```

(2) INFORMATION FOR SEQ ID NO:2:

(i) SEQUENCE CHARACTERISTICS:
      (A) LENGTH: 167 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
GGCTGTGACC CAGGGTGGGC TGTGACCCGG AGTGGGCTGT GACCCGGGGT GGGCTGTGAC      60

CCGGGTGGGC TGCGACCTGG GGTGGGCTGT GACCTGGGAT GGGCTGTGAC CCGGGTGGGC     120

TGTGACCTGG GGTGGGCTGT GACCCGGGTG GGCTGTGACC TGGGATG                   167
```

(2) INFORMATION FOR SEQ ID NO:3:

(i) SEQUENCE CHARACTERISTICS:
      (A) LENGTH: 200 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

-continued

```
GGCTGTGACC CAGGGTGGGC TGTGACCCGG AGTGGGCTGT GACCCGGGGT GGGCTGTGAC        60

CCGGGTGGGC TGCGACCTGG GGTGGGCTGT GACCTGGGAT GGGCTGTGAC CCGGGTGGGC       120

TGTGACCTGG GGTGGGCTGT GACCCGGGTG GGCTGTGACC TGGGGTGGGC TGTGACCCGG       180

GTGGGCTGTG ACCTGGGATG                                                  200
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
TGTTCCTAGT CTTACGCCAG TG                                                22
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GTCAGTATCA CAGGCTGCGA G                                                 21
```